(12) United States Patent
Sota et al.

(10) Patent No.: US 7,438,855 B2
(45) Date of Patent: Oct. 21, 2008

(54) APPARATUS FOR MEASURING GLUCOSE CONCENTRATION

(75) Inventors: Takayuki Sota, Tokyo (JP); Atsushi Nakamura, Osaka (JP); Katsuo Aizawa, Kanagawa-ken (JP); Masao Kanazawa, Tokyo (JP); Takeshi Hasegawa, Kyoto (JP)

(73) Assignees: Waseda University, Tokyo (JP); Photoscience Incorporated, Tokyo (JP)

( * ) Notice: Subject to any disclaimer, the term of this patent is extended or adjusted under 35 U.S.C. 154(b) by 433 days.

(21) Appl. No.: 10/193,229

(22) Filed: Jul. 12, 2002

(65) Prior Publication Data

US 2003/0031597 A1   Feb. 13, 2003

(30) Foreign Application Priority Data

Aug. 3, 2001   (JP)   ............................. 2001-236680

(51) Int. Cl.
*G01N 21/00* (2006.01)

(52) U.S. Cl. .................. 422/82.09; 422/99; 422/100; 422/101; 436/180; 600/310; 600/319; 700/90; 700/268

(58) Field of Classification Search .............. 422/82.09, 422/99–101; 436/180; 600/310, 319; 700/90, 700/268

See application file for complete search history.

(56) References Cited

U.S. PATENT DOCUMENTS

2003/0023152 A1* 1/2003 Abbink et al. .............. 600/316

OTHER PUBLICATIONS

Heise, Multivariate Determination of Glucose in Whole Blood by Attenuated Total Reflection Infrared Spectroscopy, Analytical Chem, 1989,61, 2009-2015.*

* cited by examiner

*Primary Examiner*—Jill Warden
*Assistant Examiner*—Jyoti Nagpaul
(74) *Attorney, Agent, or Firm*—Oblon, Spivak, McClelland, Maier & Neustadt, P.C.

(57) ABSTRACT

An apparatus for measuring a glucose concentration is non-invasive, accurate, and compact. The apparatus includes a detection unit (10) and a principal component analysis (PCA) unit (20). The detection unit includes a light source (11) to emit mid-infrared light, an ATR prism (12) to receive the mid-infrared light with a measuring object placed on the ATR prism, and a spectrum detector (13) to detect an absorption spectrum from the mid-infrared light from the ATR prism. The PCA unit includes a loading memory (24) to store a glucose corresponding loading and a personal data memory (28) to store personal data in the form of a calibration curve. According to the detected absorption spectrum, stored loading, and stored personal data, the PCA unit computes a glucose concentration of the measuring object.

2 Claims, 10 Drawing Sheets

$$\begin{bmatrix} 1.721 \times 10^{-2} \\ 1.669 \times 10^{-2} \\ 1.645 \times 10^{-2} \\ 1.655 \times 10^{-2} \end{bmatrix} \begin{bmatrix} -1.219 \times 10^{-3} \\ -5.477 \times 10^{-4} \\ 1.024 \times 10^{-3} \\ 8.030 \times 10^{-4} \end{bmatrix} \begin{bmatrix} 5.274 \times 10^{-4} \\ -7.572 \times 10^{-4} \\ 2.464 \times 10^{-4} \\ -2.990 \times 10^{-5} \end{bmatrix} \begin{bmatrix} -1.788 \times 10^{-5} \\ 5.878 \times 10^{-5} \\ 1.909 \times 10^{-4} \\ -2.304 \times 10^{-4} \end{bmatrix}$$

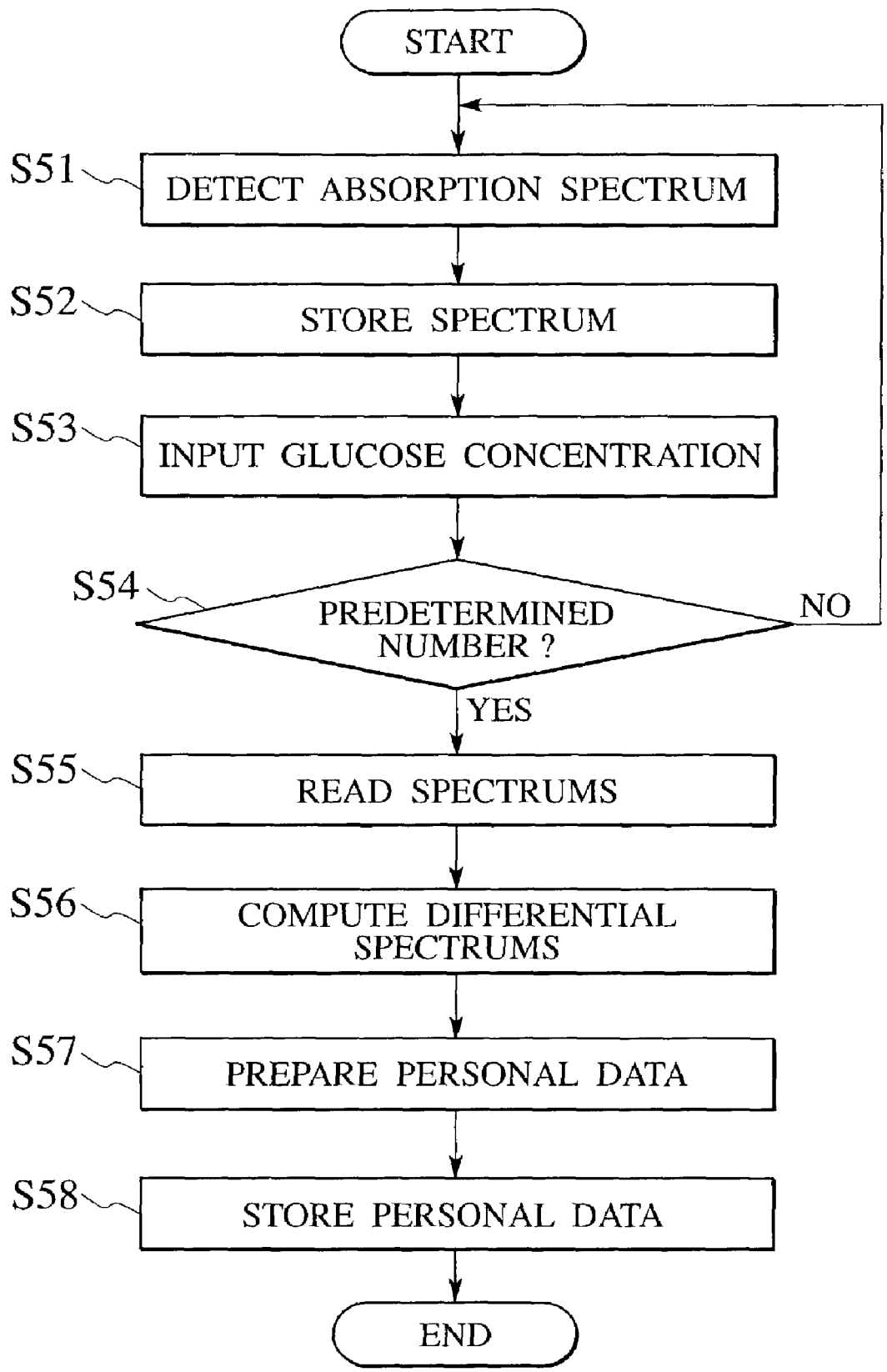

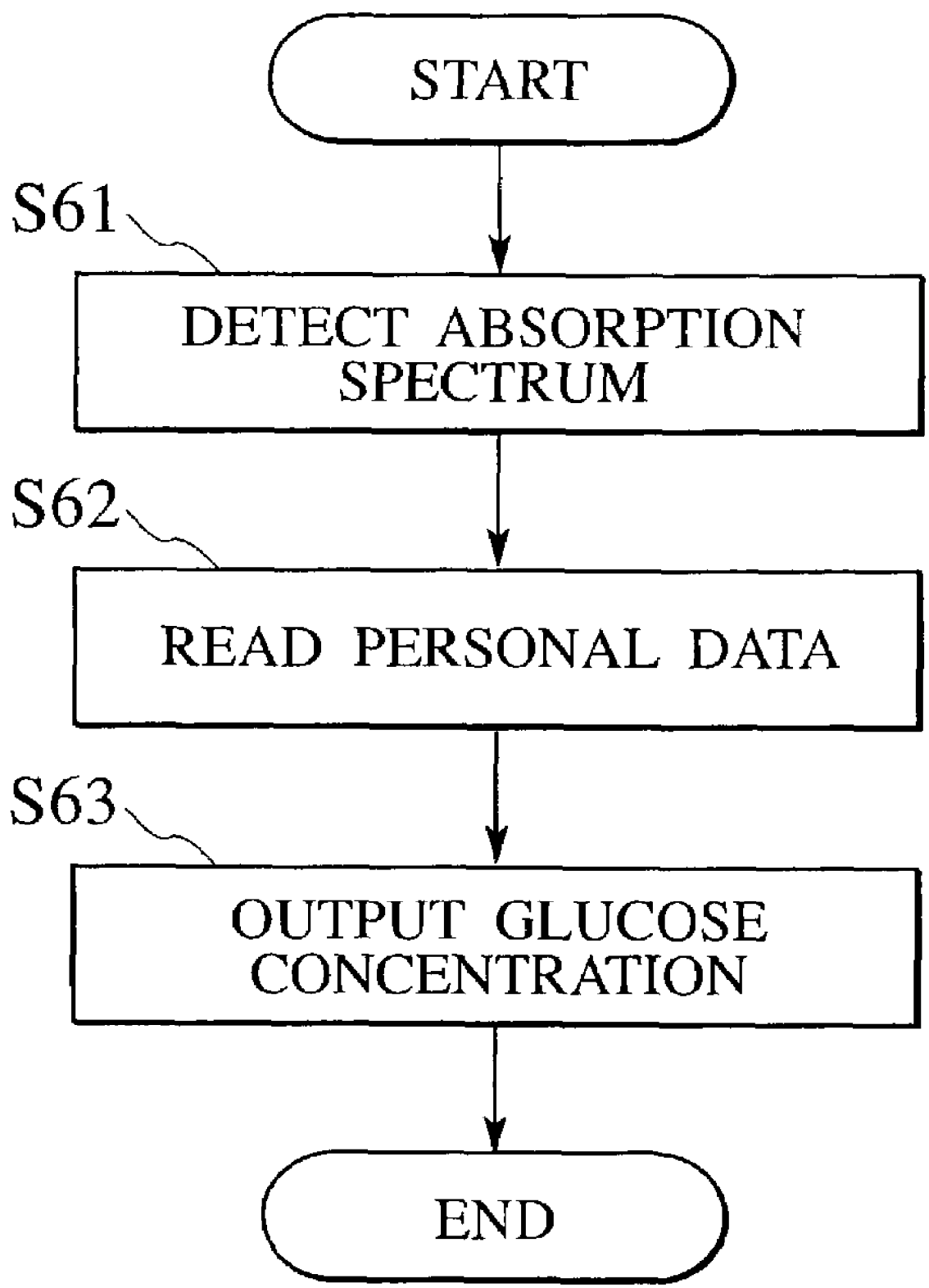

APPARATUS FOR MEASURING GLUCOSE CONCENTRATION

BACKGROUND OF THE INVENTION

1. Field of the Invention

The present invention relates to an apparatus for measuring a glucose concentration contained in a sample according to an absorption spectrum in a mid-infrared region detected from the sample.

2. Description of the Related Art

There are apparatuses for measuring a blood-sugar level (hereinafter referred to as glucose concentration) of a patient, to diagnose or cure a malady such as diabetes. Examples of such apparatuses include an automatic analyzer that automatically analyzes sampled blood and finds a glucose concentration and a simple measuring device that measures a glucose concentration from a small amount of blood collected from a patient by puncturing the fingertip or earlobe of the patient.

These apparatuses invade and pain a patient when collecting blood from the patient and involve a risk of causing infectious diseases to the patient. Such apparatuses, therefore, tend to be avoided by patients and are difficult to apply them for strictly controlling the glucose concentrations of patients.

To cope with the problems, there have been proposed apparatuses capable of measuring the glucose concentration of a patient without collecting blood from the patient and without paining or invading the patient. One of such apparatuses employs near-infrared light to percutaneously measure a glucose concentration. Some of such apparatuses have already started investigational operations in the United States.

The apparatuses employing near-infrared light, however, involve a large error of about ±20% in measured glucose concentrations and are bulky. There is a need of a glucose concentration measuring apparatus that is compact, correctly measures a glucose concentration, is noninvasive, and is usable daily by a patient to control the glucose concentration of the patient.

SUMMARY OF THE INVENTION

An object of the present invention is to provide an apparatus for measuring a glucose concentration that is noninvasive, accurate, and compact.

Desirably, according to an aspect of the present invention, an apparatus for measuring a glucose concentration includes a detection unit to detect an absorption spectrum in a mid-infrared region from a sample containing glucose, a loading computation unit to compute a loading corresponding to the glucose according to the detected absorption spectrum and a principal component analysis, and a memory to store the computed loading.

The loading is also called an abstract vector or an abstract spectrum and corresponds to an orthogonal basis of a vector space formed by an absorption spectrum.

Desirably, a measured absorption spectrum is standardized, and the standardized absorption spectrum is mapped in the direction of a loading corresponding to glucose. The quantity of the mapping is called a score. Namely, the score is an inner product of the standardized absorption spectrum and the glucose corresponding loading.

Desirably, according to another aspect of the present invention, an apparatus for measuring a glucose concentration includes detection unit to detect an absorption spectrum in a mid-infrared region from a sample containing glucose, a loading computation unit to compute a loading corresponding to the glucose according to the detected absorption spectrum and a principal component analysis, and a score determination unit to determine a score according to the detected absorption spectrum and computed loading, the score serving as a coefficient to develop the absorption spectrum into the loading.

Desirably, according to still another aspect of the present invention, the apparatus may further include a concentration determination unit to determine a glucose concentration according to a score provided by the score determination unit and a calibration curve.

Desirably, according to still another aspect of the present invention, an apparatus for measuring a glucose concentration includes a loading memory to store a loading obtained from a principal component analysis conducted on a sample, the loading corresponding to glucose contained in the sample, a calibration curve memory to store a calibration curve that relates a score to a glucose concentration, a detection unit to detect an absorption spectrum in a mid-infrared region from the sample containing glucose, a score determination unit to determine a score according to the stored loading and the detected absorption spectrum, the score serving as a coefficient to develop the absorption spectrum into the loading, and a concentration determination unit to determine a glucose concentration according to the determined score and the calibration curve.

Desirably, according to still another aspect of the present invention, the detection unit may include a nichrome wire light source, a silicon carbide light source, or a ceramic light source to emit light in a mid-infrared region and an attenuated total reflection (ATR) prism or an ATR fiber. With these parts, the detection unit detects an absorption spectrum from a sample according to an attenuated total reflection spectroscopy.

According to still another aspect of the present invention, the loading computation unit may employ a principal component analysis or a partial least square (PLS) to compute a loading corresponding to glucose.

Desirably, according to still another aspect of the present invention, the glucose concentration measuring apparatus determines a glucose spectrum according to a score, which is obtained as an inner product of an absorption spectrum detected by the detection unit and a loading corresponding to glucose.

Desirably, according to still another aspect of the present invention, the calibration curve memory may store a calibration curve indicating a relationship between glucose concentrations and scores computed according to a principal component analysis or a PLS.

Desirably, according to still another aspect of the present invention, the concentration determination unit may determine a glucose concentration by collating a score determined by the score determination unit with the calibration curve stored in the calibration curve memory.

Desirably, according to still another aspect of the present invention, an apparatus for measuring a glucose concentration includes a detection unit to detect an absorption spectrum in a mid-infrared region from a sample containing glucose, a spectrum determination unit to determine a glucose spectrum by subtracting a background substance absorption spectrum from the detected absorption spectrum, and a memory to store a calibration curve that relates the determined glucose spectrum to a glucose concentration.

Desirably, according to still another aspect of the present invention, the glucose concentration measuring apparatus may further include a concentration determination unit to determine a glucose concentration according to a glucose spectrum determined by the spectrum determination unit and the calibration curve.

BRIEF DESCRIPTION OF THE DRAWINGS

FIG. 11 is a flowchart showing a personal data setting operation carried out in the apparatus of FIG. 10; and FIG. 12 is a flowchart showing a glucose concentration measuring operation carried out in the apparatus of FIG. 10.

DETAILED DESCRIPTION OF EMBODIMENTS

Embodiments of the present invention will be explained with reference to the accompanying drawings.

Figure 1:
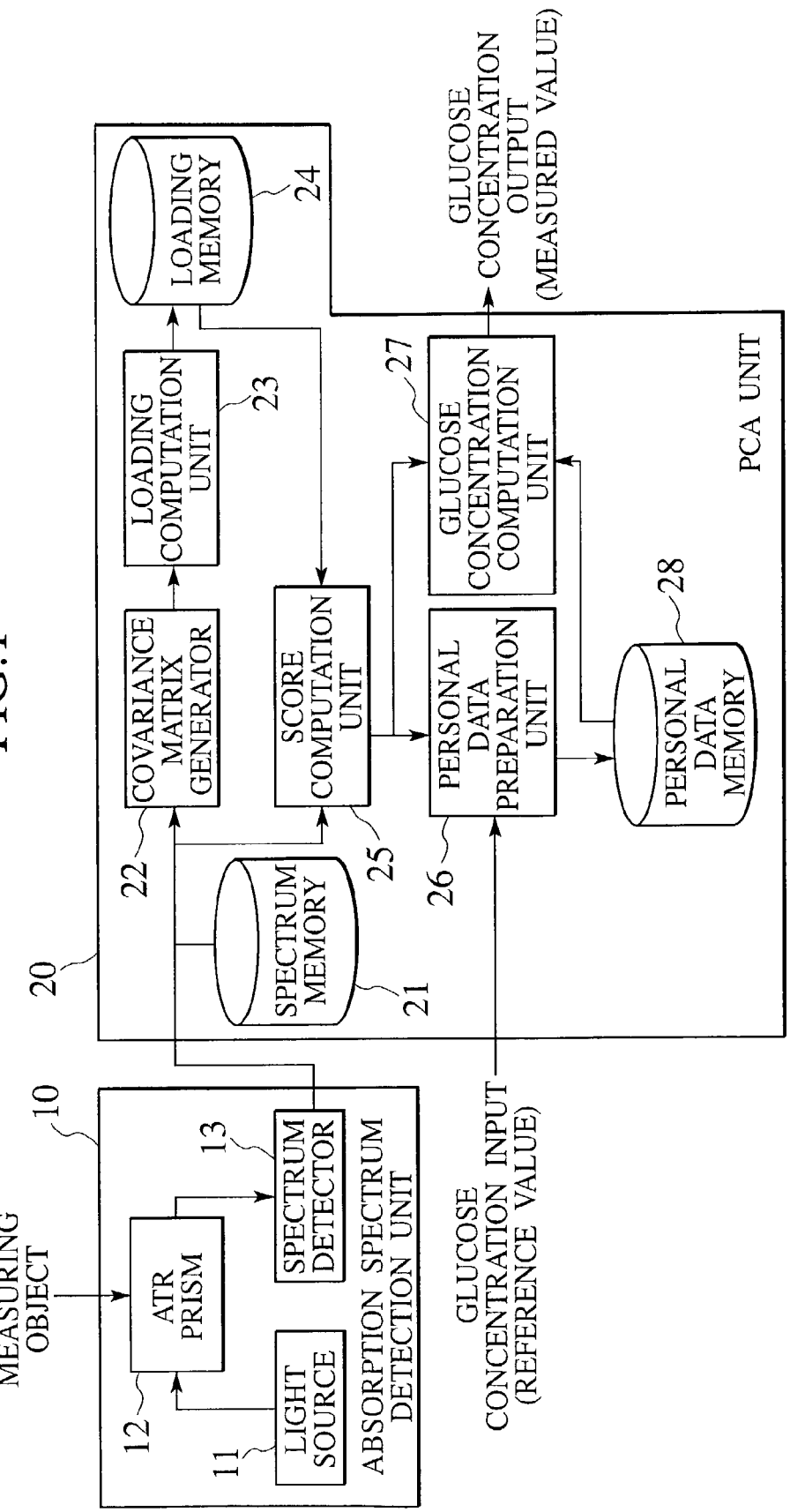
FIG. 1 is a block diagram showing an apparatus for measuring a glucose concentration according to a first embodiment of the present invention.

FIG. 1 is a block diagram showing an apparatus for measuring a glucose concentration according to the first embodiment of the present invention.

The apparatus includes a detection unit 10 and a PCA (principal component analysis) unit 20. The detection unit 10 detects an absorption spectrum in a mid-infrared region from a sample such as a finger of a patient. The PCA unit 20 measures a glucose concentration according to a multivariate PCA conducted on the absorption spectrum detected by the detection unit 10.

The detection unit 10 employs, for example, an attenuated total reflection spectroscopy to measure a mid-infrared absorption spectrum from an object that is pressed to a specific part on a main face of a casing provided for the detection unit 10. The detection unit 10 may employ mid-infrared light in a wave-number range of, for example, 750 cm$^{-1}$ to 4000 cm$^{-1}$.

The detection unit 10 includes a light source 11 to emit mid-infrared light, an attenuated total reflection (ATR) prism 12 to receive the emitted light, and a spectrum detector 13 to detect a spectrum of light absorbed by a measuring object and transmitted through the prism 12.

The light source 11 to emit mid-infrared light may be a nichrome light source, a silicon carbide light source, or a ceramic light source. The light source 11 has a given surface temperature to emit a continuous spectrum in the mid-infrared region.

The mid-infrared region is useful to directly detect absorption by normal molecular vibration of glucose. On the other hand, a near-infrared region is useful only to detect absorption by the second harmonic, third harmonics, or combination tone of glucose molecular vibration.

The prism 12 has a reflection face on which a measuring object is placed. Absorption by the measuring object is measured according to an attenuated total reflection spectroscopy.

According to the first embodiment, the apparatus measures a glucose concentration of a patient. A finger, for example, the fifth finger of the patient is pressed to the prism 12, and absorption by the skin of the finger is detected.

The prism 12 may be a single or multiple reflection prism made of, for example, ZnSe, Ge, or diamond.

Figure 2:
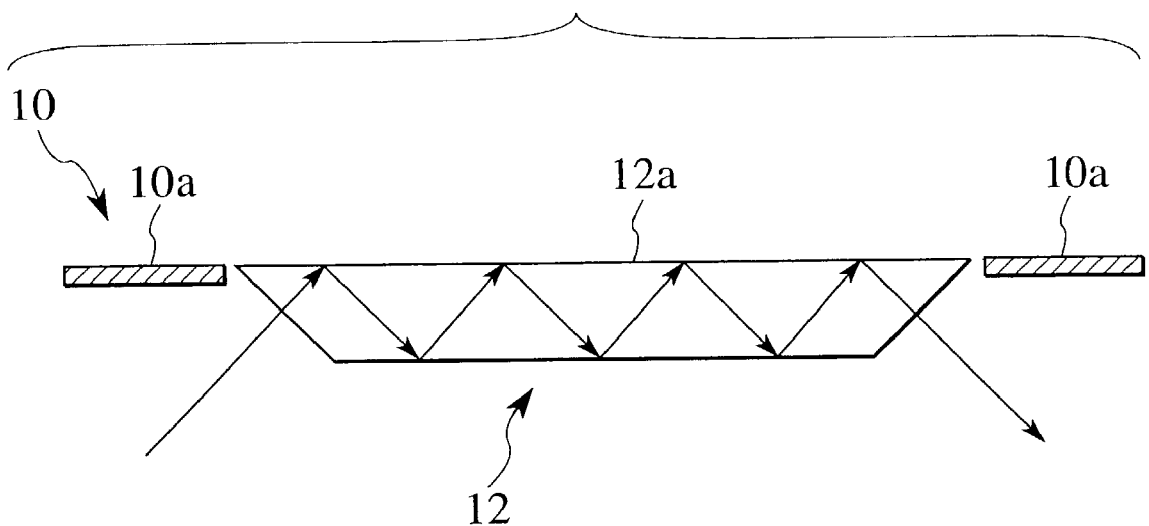
FIG. 2 is a sectional view showing an ATR prism arranged in the apparatus of FIG. 1.

FIG. 2 is a sectional view showing an example of the ATR prism 12.

The prism 12 is made of, for example, ZnSe, Ge, or diamond and has a reflection face 12a to totally reflect incident light. The reflection face 12a may be positioned in a main face 10a of a casing of the detection unit 10. Measurement is carried out by pressing, for example, a finger of a patient to the reflection face 12a.

The first embodiment uses the prism 12 to detect an absorption spectrum containing a glucose spectrum. The absorption spectrum is also obtainable by, for example, a diffused reflection method.

In FIG. 1, the spectrum detector 13 receives light from the prism 12, spectrally decomposes the received light, and detects a spectrum. The spectrum detector 13 may be a distributed infrared spectrophotometer or a Fourier infrared spectrophotometer.

To improve a detection accuracy, the detection unit 10 may detect an absorption spectrum several times and average the detected spectrums. For example, the detection unit 10 may carry out 32 detection operations and provide an average of them.

The PCA unit 20 computes a glucose concentration according to a theory "Factor Analytical Resolution of Minute Signals (FARMS)" proposed by T. Hasegawa in a report "Detection of Minute Chemical Species by Principal-Component Analysis" appeared in Anal. Chem., 71 (1999) 3085 (the entirety of which is incorporated herein by reference).

The PCA unit 20 computes glucose spectrums from a set of absorption spectrums detected by the detection unit 10 on a patient, collates the glucose spectrums with externally provided reference glucose concentrations measured on the patient, and prepares personal data in the form of a glucose concentration calibration curve specific to the patient. Once the personal data is prepared, the PCA unit 20 collates an absorption spectrum detected by the detection unit 10 from the patient with the personal data, to find a glucose concentration.

The PCA unit 20 includes a spectrum memory 21 to store absorption spectrums provided by the detection unit 10, a covariance matrix generator 22 to generate a covariance matrix, which is a kind of a correlation matrix, from a set of the absorption spectrums stored in the spectrum memory 21, and a loading computation unit 23 to compute loadings from the generated covariance matrix.

The spectrum memory 21 to store a set of absorption spectrums provided by the detection unit 10 may be a semiconductor memory.

The set of absorption spectrums form measured data A in this embodiment and are expressed in a matrix in which the absorption spectrums serve as row vectors. The number of the row vectors is equal to the number of the detected absorption spectrums. The matrix of the measured data A may contain the absorption spectrums as column vectors. In this case, the number of the column vectors is equal to the number of the absorption spectrums.

Any absorption spectrum detected by the detection unit 10 involves an influence of carbon dioxide contained in the atmosphere, which must be removed from the detected spectrum. The detected absorption spectrum also involves an influence of measuring conditions such as a finger contact state. Namely, the detected absorption spectrum varies due to pressure difference or contact area difference caused by the finger pressed to the prism 12. To remove or minimize such influences and variations, normalization is carried out by dividing the detected absorption spectrum by an integrated spectrum.

The covariance matrix generator 22 generates a covariance matrix according to the set of spectrums read out of the spectrum memory 21. Namely, the covariance matrix generator 22 generates a covariance matrix from the measured data A. A covariance matrix C is defined as follows:

$$C_{ij} = \sum_{n=1}^{N} (I_{ni} - \bar{I}_n)(I_{nj} - \bar{I}_n)/N$$

where $C_{ij}$ is an element (i, j) of the covariance matrix C, $I_{ni}$ is an "i"th component of an "n"th spectrum, $\bar{I}_n$ is an average of the "n"th spectrum, and N is the number of the spectrums.

The loading computation unit 23 computes loadings according to the generated covariance matrix.

The loading computation unit 23 computes characteristic vectors and loadings from the generated covariance matrix. The measured data A is assumed as a vector space and is decomposed. At this time, the characteristic vectors correspond to orthogonal vectors, and a characteristic value expresses the contribution of a corresponding one of the characteristic vectors to the developing of the vector space.

The PCA unit 20 also includes a loading memory 24 to store a loading corresponding to glucose among the loadings computed by the loading computation unit 23 and a score computation unit 25 to compute scores according to the loading in the loading memory 24.

The loading memory 24 to store a loading corresponding to glucose among the loadings computed by the loading computation unit 23 may be a semiconductor memory. The meaning of the loading will be explained later.

The score computation unit 25 computes scores according to the absorption spectrums in the spectrum memory 21 and the loading in the loading memory 24.

The score computation unit 25 uses the characteristic vectors to develop the measured data A as follows:

$$A = \vec{t}_1 \vec{p}_1 + \vec{t}_2 \vec{p}_2 + \ldots + \vec{t}_m \vec{p}_m = \sum_{j=1}^{m} \vec{t}_j \vec{p}_j = TP$$

where a mapping quantity vector $t_j$ is a score and an orthogonal vector $p_j$ is a loading. The score vectors are collectively expressed in a matrix T, and the loading vectors are collectively expressed in a matrix P.

The matrix P corresponds to a matrix of the found characteristic vectors. In the matrix P, the first loading $p_1$ corresponds to an average spectrum.

According to the first embodiment, glucose is a minor component in an absorption spectrum whose main components are water, protein, and lipid. According to the FARMS theory mentioned above, the second loading $p_2$ and loadings that follow correspond to the glucose. The first embodiment employs such a relationship to find a glucose concentration.

A score corresponding to a glucose concentration is obtained from an inner product of an absorption spectrum and a loading corresponding to glucose. Based on this, the score computation unit 25 computes a score corresponding to a glucose concentration. In the following explanation, a score corresponding to a glucose concentration is simply called a score.

The PCA unit 20 also includes a personal data preparation unit 26 to prepare personal data in the form of a glucose concentration calibration curve according to the scores computed by the score computation unit 25 and glucose concentrations externally entered into the PCA unit 20. The PCA unit 20 further includes a personal data memory 28 to store the prepared personal data.

The personal data preparation unit 26 uses externally input glucose concentrations as reference values and prepares a calibration curve that indicates a relationship between the scores computed by the score computation unit 25 and the externally provided glucose concentrations. The calibration curve serves as personal data.

Namely, the personal data preparation unit 26 prepares the calibration curve representing a relationship between the scores computed by the score computation unit 25 and the externally input glucose concentrations that correspond to the set of spectrums stored in the spectrum memory 21.

The personal data memory 28 stores, as personal data, the calibration curve prepared by the personal data preparation unit 26. The personal data memory 28 may be a semiconductor memory.

The PCA unit 20 further includes a glucose concentration computation unit 27 to compute a glucose concentration according to a score computed by the score computation unit 25 and the personal data stored in the personal data memory 28.

The glucose concentration computation unit 27 reads the personal data, i.e., the calibration curve from the personal data memory 28 and determines a glucose concentration corresponding to a score computed by the score computation unit 25. The glucose concentration computation unit 27 provides the determined glucose concentration as a measured glucose concentration from the PCA unit 20.

The apparatus of the first embodiment is noninvasive because it measures a glucose concentration on a measuring object pressed to the prism 12. The apparatus employs compact parts for the detection unit 10 and a semiconductor integrated circuit for the PCA unit 20, to thereby minimize the total size of the apparatus.

A glucose concentration measuring operation according to the first embodiment will be explained.

Figure 3:
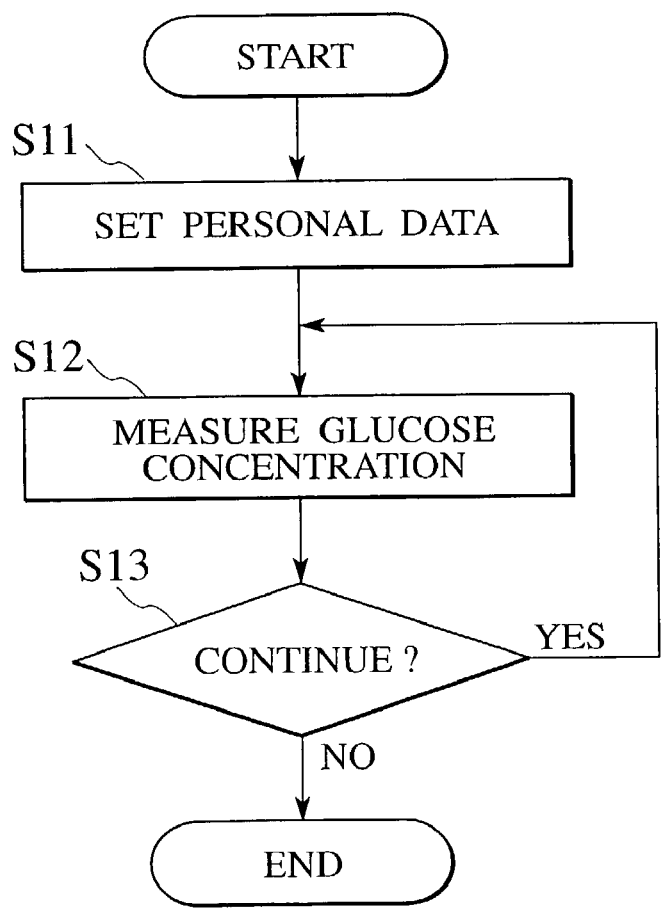
FIG. 3 is a flowchart showing a glucose concentration measuring operation carried out in the apparatus of FIG. 1.

FIG. 3 is a flowchart showing a glucose concentration measuring flow carried out in the apparatus of the first embodiment of FIG. 1.

Step S11 sets personal data in the apparatus. This is done by asking a patient to orally take glucose and by measuring glucose concentrations in the blood of the patient at given intervals.

For example, the patient orally takes a given dose of glucose, and glucose concentrations in the blood of the patient are measured at given intervals with the use of, for example, a simple glucose concentration measuring device that is separately prepared in addition to the apparatus of the first embodiment. At the same time, the detection unit 10 is used to measure absorption spectrums from the patient. The glucose concentrations measured at the given intervals with the simple glucose concentration measuring device are entered into the apparatus of the first embodiment with the use of, for example, push buttons on the apparatus and are used as reference values.

The glucose concentration of the patient decreases as time passes. Measuring the glucose concentration of the patient several times at regular intervals will provide a relationship between different glucose concentrations and absorption spectrums of the patient. Personal data thus obtained is stored in the personal data memory 28 of the PCA unit 20. The personal data is in the form of a calibration curve indicating a relationship between glucose concentrations and scores in connection with the patient.

In step S12, the apparatus employs the personal data set in step S11 and measures a glucose concentration of the patient. The personal data used for measuring a glucose concentration is only for the patient who was measured in step S11. Namely, each patient has his or her own personal data. Accordingly, a specific piece of personal data is effective for measuring glucose concentrations on the person from whom the personal data was prepared.

Step S12 refers to an absorption spectrum measured with the detection unit 10 and the personal data set in step S11, to compute a glucose concentration. The details of the glucose concentration measurement will be explained later.

Step S13 determines whether or not the glucose concentration measurement of step S12 must be continued. If it must be continued, step S12 is carried out to repeat the glucose concentration measurement with the personal data set in step S11. If the measurement is not continued, the flow ends.

The apparatus may automatically repeat the glucose concentration measurement of step S12 and may terminate and initialize the measuring flow if, for example, a rest button is pushed.

Figure 4:
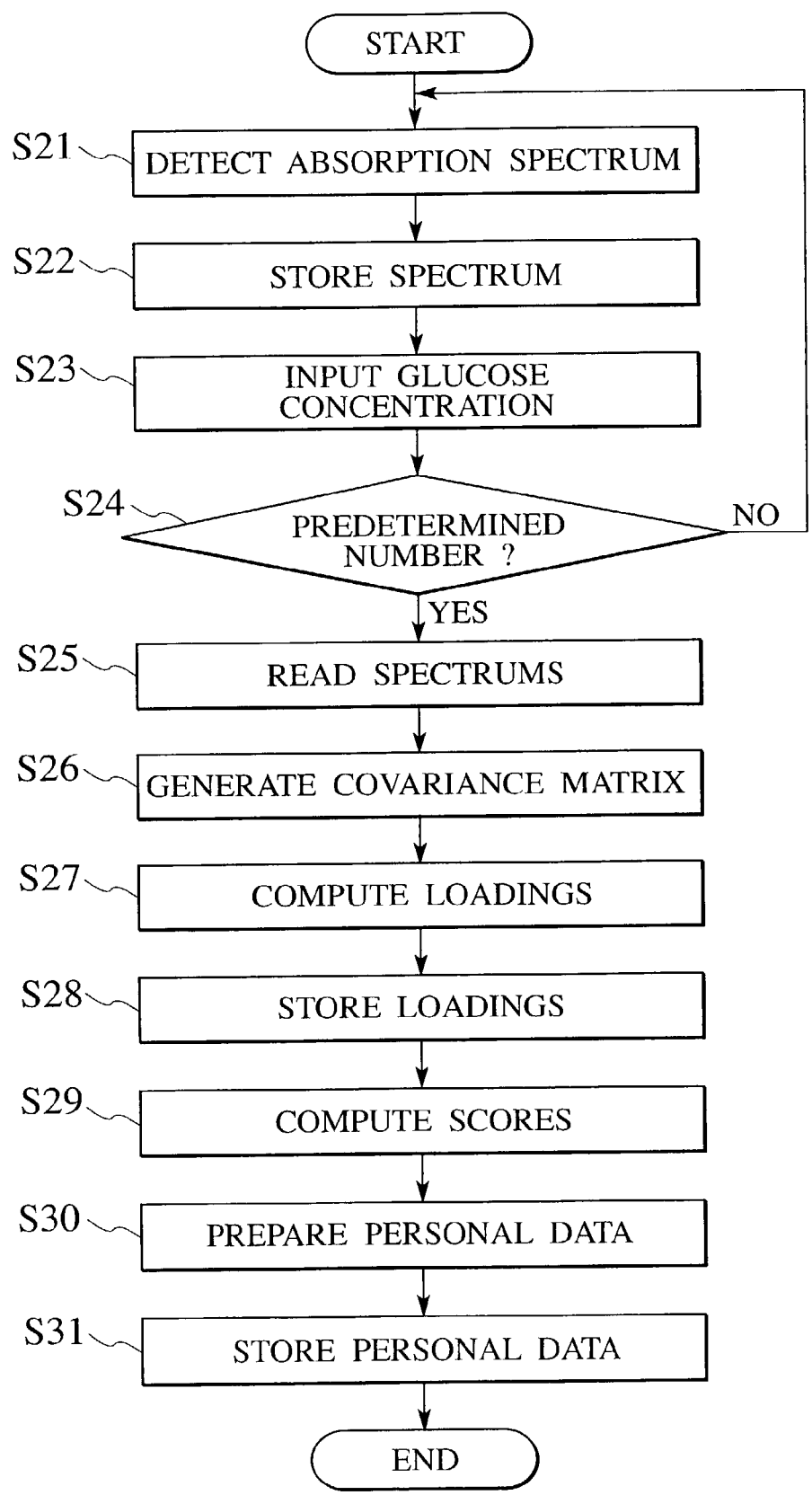
FIG. 4 is a flowchart showing a personal data setting operation carried out in the flow of FIG. 3.

FIG. 4 is a flowchart showing the details of the personal data setting operation of step S11 of FIG. 3.

In the flow of FIG. 4, the patient orally takes glucose, a predetermined number of absorption spectrums are detected from the patient, and at each detection of absorption spectrum, a glucose concentration of the patient is measured with, for example, a simple glucose concentration measuring device. The measured glucose concentration is entered into the PCA unit 20. The measured glucose concentrations were, in a test carried out according to the first embodiment, 201 mg/100 mL before taking glucose and 271 mg/100 mL, 410 mg/100 mL, and 352 mg/100 mL after taking glucose. The glucose concentration of a patient after taking glucose changes as time passes.

In step S21, the detection unit 10 detects an absorption spectrum from the patient. A measuring object, for example, a finger of the patient is pressed to the reflection face 12a of the prism 12, and the light source 11 emits mid-infrared light. The emitted light is absorbed by the measuring object on the reflection face 12a of the prism 12.

The spectrum detector 13 receives the light from the reflection face 12a of the prism 12 after the absorption by the measuring object (the finger of the patient) and detects a spectrum from the received light.

From the detected spectrum, an influence of carbon dioxide contained in the atmosphere and an influence of measuring conditions such as a contact state of the measuring object on the prism 12 are removed by, for example, normalization.

In step S22, the PCA unit 20 receives the absorption spectrum from the detection unit 10 and stores the same in the spectrum memory 21.

In step S23, a glucose concentration measured on the patient with another device is entered into the PCA unit 20. The entered glucose concentration serves as a reference value and is transferred to the personal data preparation unit 26.

Step S24 checks to see if the number of pairs each consisting of an absorption spectrum detected in step S21 and a glucose concentration entered in step S23 has reached a predetermined number.

If the number of pairs is equal to the predetermined number, step S25 is carried out, and if not, step S21 is repeated to further obtain an absorption spectrum and a corresponding glucose concentration.

In step S25, the PCA unit 20 reads a set of the spectrums stored in the spectrum memory 21 and transfers the spectrum set to the covariance matrix generator 22.

Figures 5, 6:
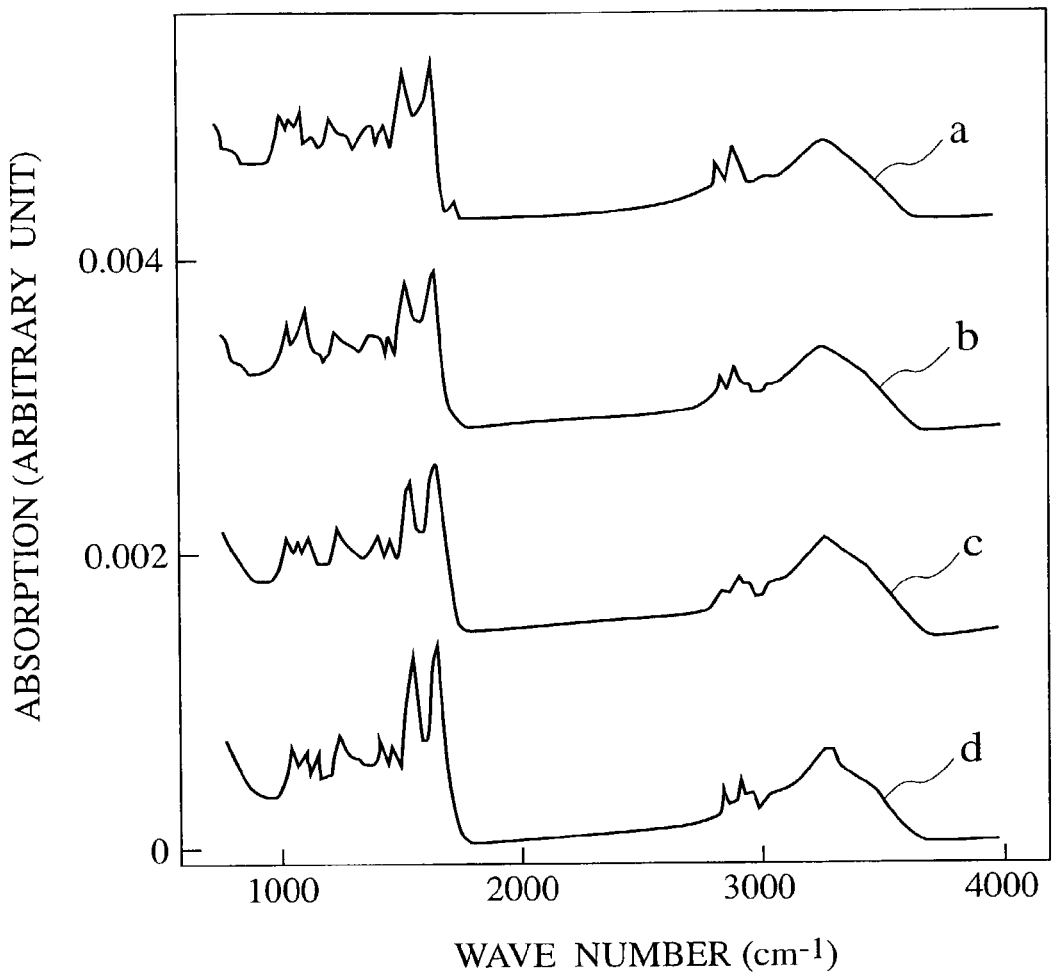
FIG. 5 shows a set of spectrums read out of a spectrum memory in the apparatus of FIG. 1.
FIG. 6 shows examples of scores computed by the apparatus of FIG. 1.

FIG. 5 shows examples of the spectrums stored in the spectrum memory 21.

Spectrums a, b, c, and d in FIG. 5 correspond to the glucose concentrations of 410 mg/100 mL, 352 mg/100 mL, 271 mg/100 mL, and 201 mg/100 mL, respectively. Each spectrum was prepared by measuring 1671 wave numbers in the range of 750 $cm^{-1}$ to 4000 $cm^{-1}$. An ordinate in FIG. 5 represents the intensity levels (with arbitrary unit) of the absorption spectrums.

In step S26, the covariance matrix generator 22 uses the set of spectrums read out of the spectrum memory 21 and generates a covariance matrix.

In step S27, the loading computation unit 23 in the PCA unit 20 uses the generated covariance matrix and computes loadings.

Namely, the loading computation unit 23 computes characteristic values and characteristic vectors from the covariance matrix. The characteristic values of the covariance matrix are as follows:

$(1.119 \times 10^{-3}, 3.478 \times 10^{-6}, 9.132 \times 10^{-7}, 9.331 \times 10^{-8})$ Percentages of the characteristic values are as follows:

$(9.9608 \times 10^{-1}, 3.0961 \times 10^{-3}, 3.1289 \times 10^{-4}, 8.3060 \times 10^{-5})$ These percentages indicate the contribution levels of characteristic vectors to the developing of a space.

The loading computation unit 23 finds characteristic vectors corresponding to the characteristic values and provides the characteristic vectors as loadings corresponding to the spectrums stored in the spectrum memory 21. The number of the loadings is equal to the number of the characteristic values.

According to the first embodiment, the loadings provided by the loading computation unit 23 rarely contain a loading that correctly matches a glucose spectrum. This is because the spectrums in the spectrum memory 21 reflect a variety of components. There is, however, at least one loading that reflects glucose. To find such a glucose corresponding loading, the loadings provided by the loading computation unit 23 are used to compute scores on the spectrums.

In step S27, the loading computation unit 23 computes loadings according to a principal component analysis. The loadings may be computed according to PLS (partial least square) that decomposes the spectrums based on known glucose concentrations. In this case, the loading computation unit 23 receives the absorption spectrums from the spectrum memory 21 and the glucose concentrations externally measured for the absorption spectrums and carries out PLS operations.

Namely, the loading computation unit 23 employs the PLS to decompose a given spectrum with the use of a corresponding glucose concentration and compute a loading directly related to the glucose concentration. At this time, the PLS provides a PLS loading indicating a common part of the absorption spectrum and a weight loading indicating an absorption spectrum corresponding to a glucose concentration change. The loading computation unit 23 employs the latter.

The loading (weight loading) provided by the PLS directly relates to the glucose concentration, and therefore, is expected to provide a high accuracy. The loading provided by the PLS may be used together with or instead of the loading provided by the PCA mentioned above.

In step S28, the loading memory 24 stores the loadings computed by the loading computation unit 23.

In step S29, the score computation unit 25 computes a score for each spectrum and each loading according to the set of spectrums stored in the spectrum memory 21 and the loadings stored in the loading memory 24.

FIG. 6 shows examples of scores computed for each of the loadings. The number of scores computed for each loading is equal to the number of the spectrums stored in the spectrum memory 21. The first to fourth components of each vector correspond to the actually measured glucose concentrations of 201 mg/100 mL, 271 mg/100 mL, 410 mg/100 mL, and 352 mg/100 mL, respectively.

According to the first embodiment, a loading whose scores are adopted for measuring the glucose concentration of a patient is dependent on the patient. Typically, scores computed from a loading corresponding to the second or third largest characteristic value show a good correlation with actually measured glucose concentrations.

Figure 7:
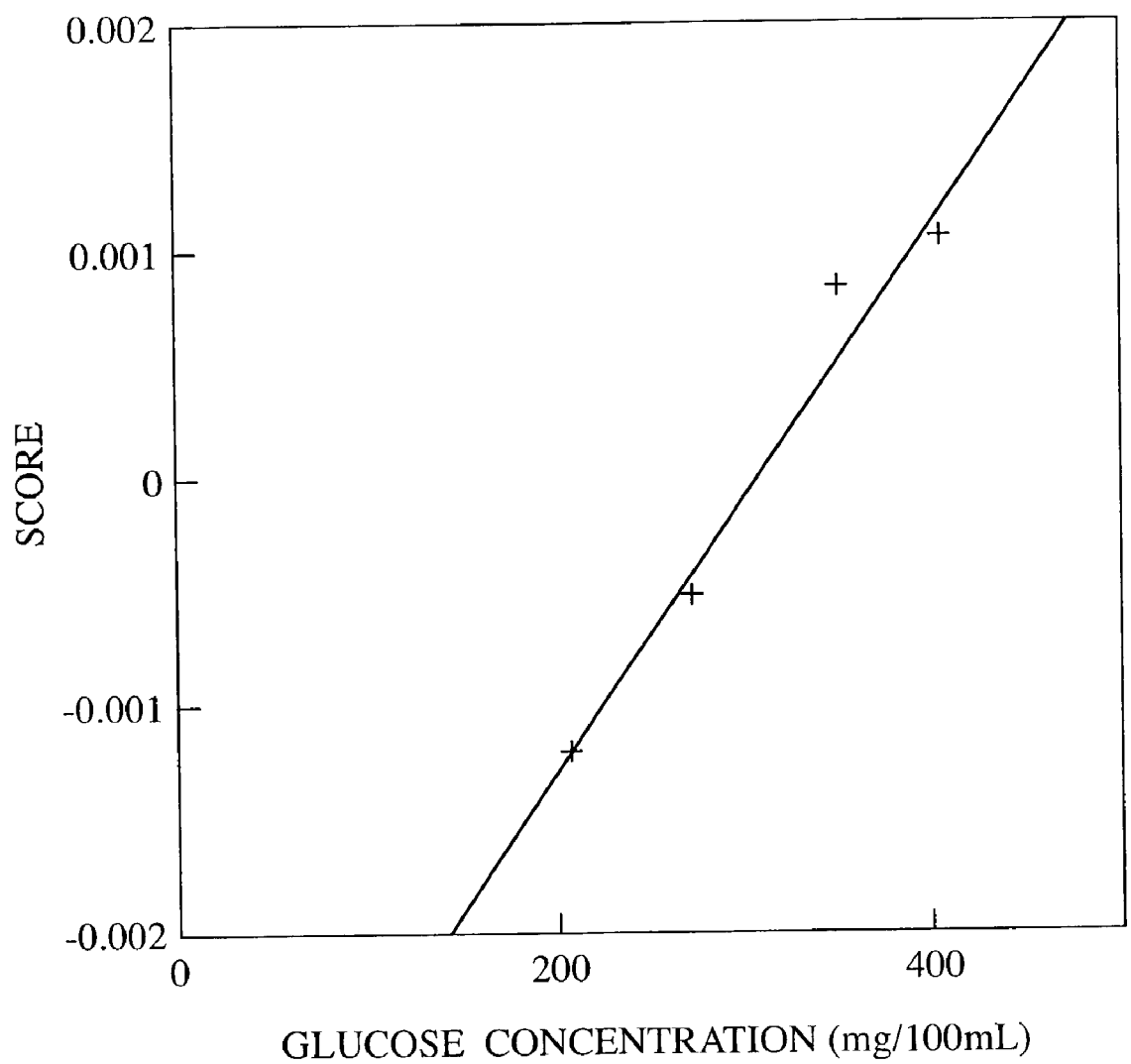
FIG. 7 shows an example of a personal calibration curve prepared by the apparatus of FIG. 1.

FIG. 7 shows a relationship between the computed scores and the actually measured glucose concentrations in connection with the patient in question. The scores have been computed from the second loading. The relationship between the glucose concentrations and the scores clearly shows linearity.

In step S30, the personal data preparation unit 26 prepares a calibration curve according to a linear approximation or a least squares method, the calibration curve indicating the relationship between the scores computed by the score computation unit 25 for the spectrums stored in the spectrum memory 21 and the externally provided glucose concentrations for the spectrums.

In step S31, the personal data memory 28 stores, as personal data, the calibration curve prepared by the personal data preparation unit 26.

Figure 8:
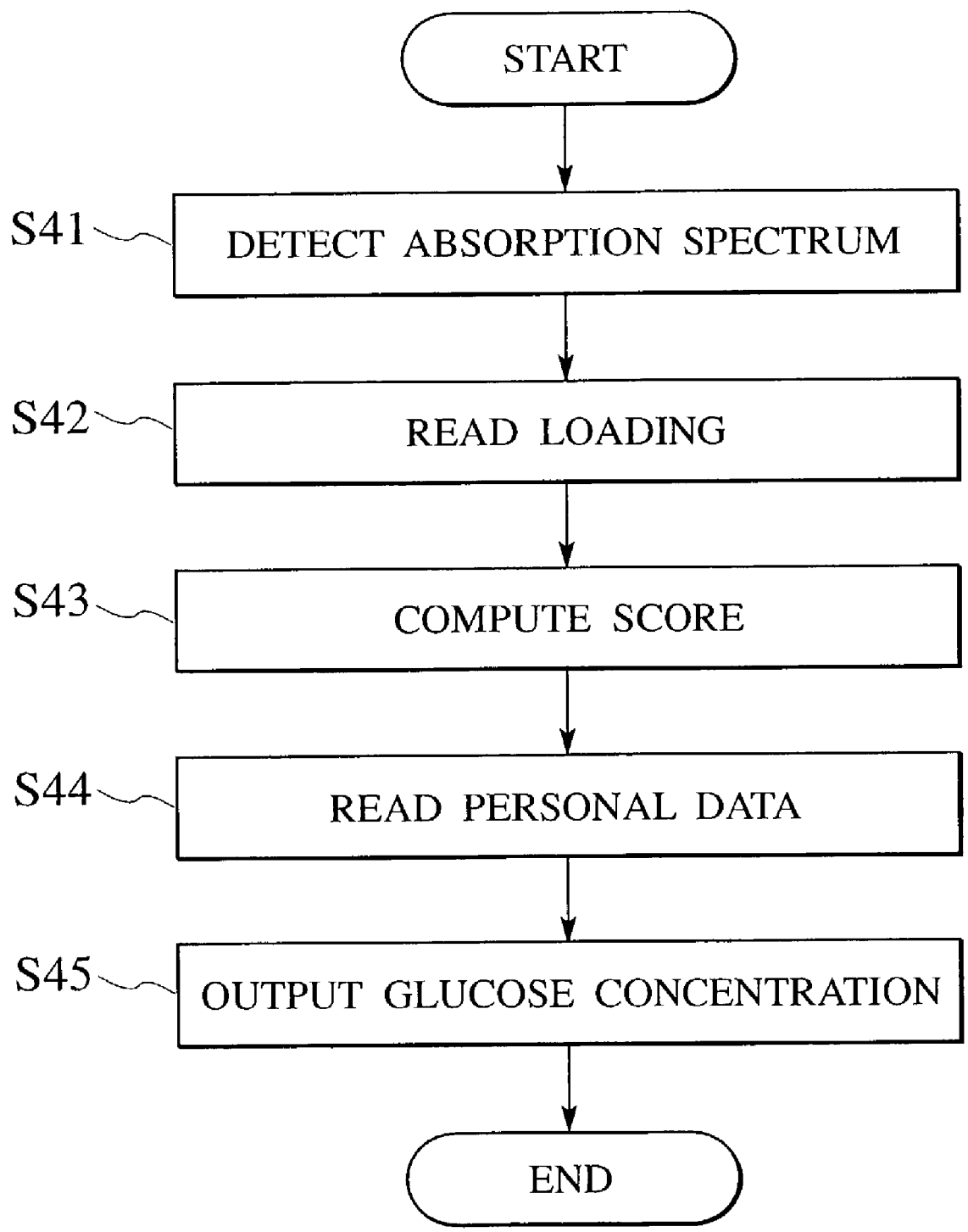
FIG. 8 is a flowchart showing a glucose concentration measuring operation carried out in the flow of FIG. 3.

FIG. 8 is a flowchart showing the details of the glucose concentration measuring operation of step S12 of FIG. 3.

In step S41, the detection unit 10 detects an absorption spectrum like step S21 of FIG. 4.

In step S42, the PCA unit 20 reads the second loading from the loading memory 24 and transfers the second loading to the score computation unit 25. The second loading is adopted because it is appropriate for the patient measured in the first embodiment.

In step S43, the score computation unit 25 computes a score according to the absorption spectrum detected by the detection unit 10 in step S41 and the second loading read from the loading memory 24 in step S42.

In step S44, the PCA unit 20 reads the personal data, i.e., the calibration curve from the personal data memory 28 and transfers the same to the glucose concentration computation unit 27. The calibration curve is the one shown in FIG. 7 and indicates a relationship between glucose concentrations and scores.

In step S45, the glucose concentration computation unit 27 refers to the personal data read from the personal data memory 28 in step S44 and computes a glucose concentration for the score computed by the score computation unit 25 in step S43. The computed glucose concentration is output as a measured glucose concentration from the apparatus of the first embodiment.

Figure 9:
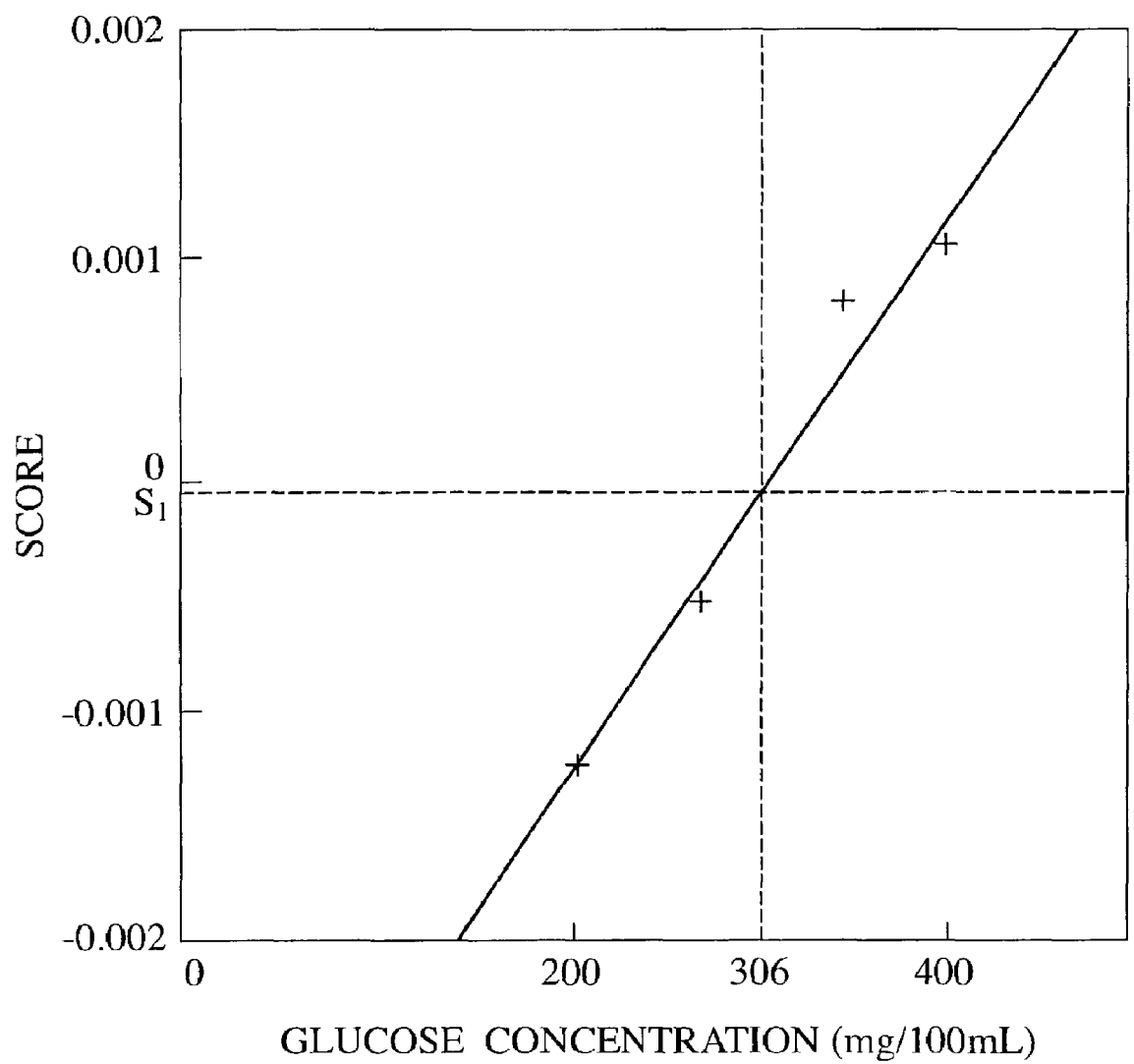
FIG. 9 explains a glucose concentration found by collating a score with the personal calibration curve of FIG. 7.

FIG. 9 shows a glucose concentration found by collating a score with the calibration curve of FIG. 7. A score $S_1$ in FIG. 9 is computed in step S43. A glucose concentration corresponding to the score $S_1$ is obtained as 306 mg/100 mL from the calibration curve of FIG. 7.

At this time, an actually measured glucose concentration was 358 mg/100 mL. Namely, the glucose concentration found in FIG. 9 according to the first embodiment involves an error of −14.5%. This error of the first embodiment shows a great improvement from the error of ±20% of the related art.

The spectrum memory 21, covariance matrix generator 22, loading computation unit 23, and personal data preparation unit 26 in the PCA unit 20 are used only when computing a glucose corresponding loading and preparing personal data, i.e., a calibration curve. If the glucose corresponding loading and calibration curve are externally provided for a patient whose glucose concentration is going to be measured, these parts 21, 22, 23, and 26 will be omitted from the apparatus of the first embodiment.

Such externally provided glucose corresponding loading and calibration curve may be measured beforehand in, for example, a hospital and may be stored in a card medium, which is read by the apparatus of the first embodiment. This arrangement makes the apparatus more compact than that of FIG. 1, and therefore, may easily be used at home.

An apparatus for measuring a glucose concentration according to the second embodiment of the present invention will be explained.

The second embodiment employs a differential spectrum method proposed by P. R. Griffiths and J. A. de Haseth in "Fourier Transform Infrared Spectroscopy," Wiley-Interscience, New York, 1986 (the entirety of which is incorporated herein by reference).

Figure 10:
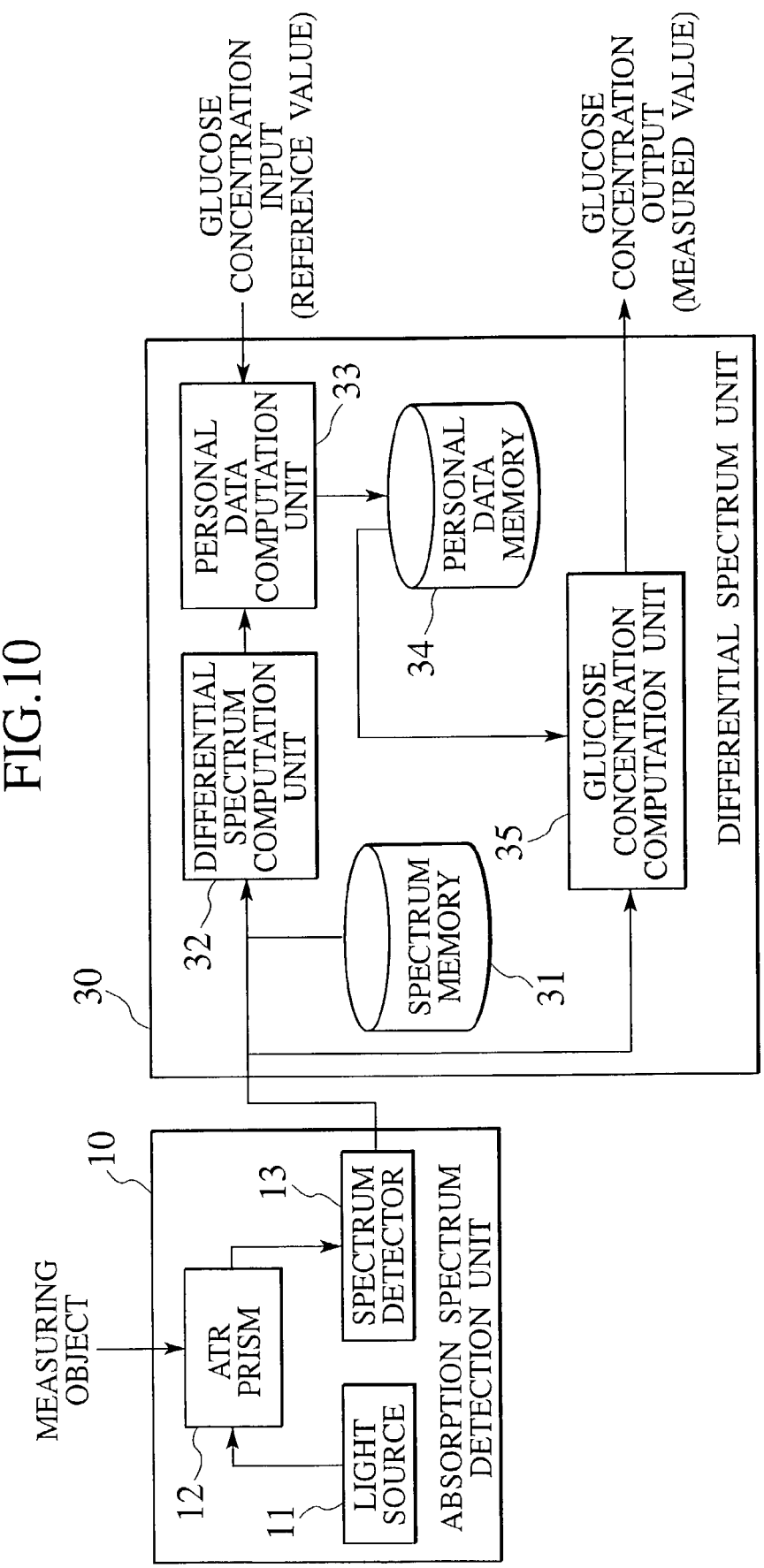
FIG. 10 is a block diagram showing an apparatus for measuring a glucose concentration according to a second embodiment of the present invention employing a differential spectrum technique.

FIG. 10 is a block diagram showing the apparatus according to the second embodiment.

This apparatus has a detection unit 10 to detect an absorption spectrum from a measuring object and a differential spectrum unit 30 to measure a glucose concentration from a differential spectrum that is obtained from the absorption spectrum detected by the detection unit 10.

The detection unit 10 of FIG. 10 has the same structure as the detection unit 10 of FIG. 1, and therefore, like parts are represented with like reference numerals to omit their explanations.

The differential spectrum unit 30 includes a spectrum memory 31 to store a set of spectrums detected by the detection unit 10 and a differential spectrum computation unit 32 to compute differential spectrums from the set of spectrums stored in the spectrum memory 31.

The spectrum memory 31 to store a set of spectrums detected by the detection unit 10 may be a semiconductor memory.

The differential spectrum computation unit 32 computes differential spectrums based on the set of spectrums stored in the spectrum memory 32. Namely, the differential spectrum computation unit 32 finds a difference between an absorption spectrum and a spectrum corresponding to a reference glucose concentration and determines a glucose spectrum that is free from an influence of background substance.

The differential spectrum unit 30 also includes a personal data computation unit 33 to compute personal data from the differential spectrums computed by the differential spectrum computation unit 32 and glucose concentrations externally input for the spectrums stored in the spectrum memory 31, and a personal data memory 34 to store the personal data computed by the personal data computation unit 33.

The personal data computation unit 33 prepares the personal data in the form of a calibration curve indicating a relationship between the differential spectrums computed by the differential spectrum computation unit 32 and the externally input glucose concentrations.

The personal data memory 34 to store the personal data computed by the personal data computation unit 33 may be a semiconductor memory.

The differential spectrum unit 30 further includes a glucose concentration computation unit 35 to compute a glucose concentration according to an absorption spectrum detected by the detection unit 10 and the personal data stored in the personal data memory 34.

The glucose concentration computation unit 35 reads an absorption spectrum detected by the detection unit 10 and the personal data, i.e., the calibration curve stored in the personal data memory 34. The unit 35 computes a glucose concentration for a differential spectrum that corresponds to the detected absorption spectrum. The computed glucose concentration is provided as a measured glucose concentration from the apparatus of the second embodiment of FIG. 10.

The apparatus of the second embodiment carries out glucose concentration measurement by pressing a measuring object to an ATR prism 12 of the detection unit 10, and therefore, is noninvasive. The second embodiment employs compact parts for the detection unit 10 and a semiconductor integrated circuit for the differential spectrum unit 30, to thereby minimize the total size of the apparatus.

A glucose concentration measuring flow according to the second embodiment will be explained.

A general flow of the second embodiment is the same as that of the first embodiment of FIG. 3. Namely, step S11 sets personal data. Based on the personal data, a glucose concentration measurement of step S12 is repeated.

FIG. 11 shows the details of the personal data setting operation according to the second embodiment.

In step S51, the detection unit 10 detects an absorption spectrum from a measuring object such as a finger of a patient. In step S52, the spectrum memory 31 of the differential spectrum unit 30 stores the spectrum detected by the detection unit 10. In step S53, a glucose concentration measured with an external device is input into the differential spectrum unit 30.

In step S54, the differential spectrum unit 30 checks to see if the number of pairs each consisting of an absorption spectrum detected in step S51 and stored in the spectrum memory 31 and a reference glucose concentration externally provided in step S53 has reached a predetermined number. If the number of pairs is equal to the predetermined number, step S55 is carried out, and if not, step S51 is repeated. Steps S51 to S54 are the same as steps S21 to S24 of FIG. 4.

In step S55, the differential spectrum unit 30 reads a set of the spectrums stored in the spectrum memory 31 and transfers them to the differential spectrum computation unit 32.

In step S56, the differential spectrum computation unit 32 computes differential spectrums by subtracting spectrums corresponding to the reference glucose concentrations from the set of spectrums read out of the spectrum memory 31.

In step S57, the personal data computation unit 33 prepares personal data, i.e., a calibration curve indicating a relationship between the differential spectrums computed by the differential spectrum computation unit 33 and the glucose concentrations externally provided for the spectrums.

In step S58, the personal data memory 34 stores the personal data computed by the personal data computation unit 33.

FIG. 12 is a flowchart showing a glucose concentration measuring operation according to the second embodiment.

In step S61, the detection unit 10 detects an absorption spectrum from the measuring object.

In step S62, the differential spectrum unit 30 reads the personal data from the personal data memory 34 and transfers the same to the glucose concentration computation unit 35.

In step S63, the glucose concentration computation unit 35 collates the absorption spectrum detected by the detection unit 10 with the personal data, i.e., the calibration curve read out of the personal data memory 34 and computes a glucose concentration. The computed glucose concentration is output as a measured glucose concentration from the apparatus of the second embodiment.

The embodiments explained above must be considered as illustrative and not restrictive. For example, the ATR prism 12 in the detection unit 10 may be an ATR fiber to which a measuring object such as the palm of the hand of a patient is pressed to measure a percutaneous absorption spectrum.

Instead of the covariance matrix employed in the first embodiment, the present invention may employ another correlation matrix such as a correlation coefficient matrix.

The present invention may be embodied in other forms without departing from the spirit or essential characteristics thereof. For example, the glucose concentration measuring apparatus of any one of the embodiments may be combined with an automatic insulin instillator, to automatically control the glucose concentration of a patient.

As explained above, the glucose concentration measuring apparatus according to the present invention is compact and capable of correctly measuring a glucose concentration of a patient in a noninvasive manner without paining the patient.

Namely, the apparatus of the present invention can measure a glucose concentration of a patient only by placing a finger or the palm of the hand of the patient on the apparatus without paining the patient and without infecting the patient with diseases. In addition, the apparatus of the present invention allows a patient, who tends to avoid severe glucose control, to strictly control his or her glucose concentration easily by himself or herself.

The entire contents of Japanese Patent Application P2001-236680 (filed Aug. 3, 2001) are incorporated herein by reference.

Although the invention has been described above by reference to certain embodiments of the invention, the invention is not limited to the embodiments described above. Modifications and variations of the embodiments described above will occur to those skilled in the art, in light of the above teachings. The scope of the invention is defined with reference to the following claims.

What is claimed is:

1. An apparatus for measuring glucose concentration, the apparatus comprising:
    a device to detect an absorption spectrum in a mid-infrared region corresponding to each of a plurality of samples of a patient multiple times over a time period, the device configured to conduct optical measurements on the patient, in order to obtain a calibration curve;
    a device to calculate the glucose concentration of each of the samples from said absorption spectra;
    a device to produce a covariance matrix based on the plurality of absorption spectrums;

a device to obtain a plurality of eigenvectors having a relatively large eigenvalue from the covariance matrix, and set these as the spectrum loading vectors for principal component analysis;

a device to take the inner product of the absorption spectrums of each of the samples and the plurality of spectrum loading vectors and obtain a plurality of spectrum score vectors of principal component analysis corresponding to each of the spectrum loading vectors;

a device to obtain from among the plurality of spectrum score vectors, the single spectrum score vector in that each of the components have the best correlative relationship to the plurality of glucose concentrations measured;

a device to store the relationship of the spectrum score vector and the glucose concentration as a calibration curve, and store the single spectrum loading vector corresponding to the spectrum score vector;

a device to read the calibration curve; and a device to determine a glucose concentration of an sample as the detected result based on the computed spectrum score and the calibration curve.

2. An apparatus for measuring a glucose concentration, comprising:

a detection unit configured to detect an absorption spectrum in a mid-infrared region from the blood of a patient containing glucose through a percutaneous route non-invasively;

a spectrum loading computation unit configured to compute a spectrum loading corresponding to the glucose absorption spectrum using the detected absorption spectrum and a principal component analysis of the detected absorption spectrum;

a spectrum score determination unit configured to determine a spectrum score according to the detected absorption spectrum and computed spectrum loading, the spectrum score serving as a coefficient to develop the absorption spectrum into the spectrum loading; and a memory configured to store a calibration curve that relates the determined spectrum score to a glucose concentration.

* * * * *